United States Patent [19]

Dragisich

[11] Patent Number: 5,414,112
[45] Date of Patent: May 9, 1995

[54] N-BIS(PHOSPHONOMETHYL) AMINO ACIDS AND THEIR USE AS SCALE INHIBITORS

[75] Inventor: Vera Dragisich, Lisle, Ill.

[73] Assignee: Nalco Chemical Company, Naperville, Ill.

[21] Appl. No.: 149,652

[22] Filed: Nov. 9, 1993

[51] Int. Cl.6 ............................................. C07F 9/38
[52] U.S. Cl. ........................................ 562/12; 562/14
[58] Field of Search ............... 562/562, 567, 568, 12, 562/14; 564/15

[56] References Cited

U.S. PATENT DOCUMENTS 3,288,846 11/1966 Irani et al. .
3,434,969 3/1969 Ralston ................................ 210/58
4,047,927 9/1977 Gaertner et al. ........................ 71/86
4,307,038 12/1981 Sommer et al. ................... 260/502.5
4,308,147 12/1981 Sommer et al. ..................... 210/700
5,087,376 2/1992 Bendiksen et al. .

OTHER PUBLICATIONS

Chemical Abstracts Online 120:166669 Jun. 8, 1993.
Chemical Abstracts Online 119:259403 Feb. 5, 1993.

Primary Examiner—José G. Dees
Assistant Examiner—Samuel Barts
Attorney, Agent, or Firm—Robert A. Miller; James J. Drake

[57] ABSTRACT

Certain N-bis(phosphonomethyl) amino acids are novel compounds and are useful in preventing calcium carbonate scale.

2 Claims, 1 Drawing Sheet

N-BIS(PHOSPHONOMETHYL) AMINO ACIDS AND THEIR USE AS SCALE INHIBITORS

BACKGROUND OF THE INVENTION

Most industrial waters contain alkaline earth metal cations, such as calcium, barium, magnesium, etc. and several anions such as bicarbonate, carbonate, sulfate, oxalate, phosphate, silicate, fluoride, etc. When combinations of these anions and cations are present in concentrations which exceed the solubility of their reaction products, precipitates form until these product solubility concentrations are no longer exceeded. For example, when the concentrations of calcium ion and carbonate ion exceed the solubility of the calcium carbonate reaction products, a solid phase of calcium carbonate will form. Calcium carbonate is the most common form of scale.

Solubility product concentrations are exceeded for various reasons, such as partial evaporation of the water phase, change in pH, pressure or temperature, and the introduction of additional ions which form insoluble compounds with the ions already present in the solution.

As these reaction products precipitate on surfaces of the water carrying system, they form scale or deposits. This accumulation prevents effective heat transfer, interferes with fluid flow, facilitates corrosive processes and harbors bacteria. This scale is an expensive problem in many industrial water systems causing delays and shutdowns for cleaning and removal.

Scale-forming compounds can be prevented from precipitating by inactivating their cations with chelating or sequestering agents, so that the solubility of their reaction products is not exceeded. Generally, this requires as much chelating or sequestering agent as cation, since chelation is a stoichiometric reaction, and these amounts are not always desirable or economical.

Almost 50 years ago, it was discovered that certain inorganic polyphosphates would prevent such precipitation when added in amounts far less than the concentrations needed for sequestering or chelating. By polyphosphates, we mean phosphates having a molar ratio of metal oxide: $P_2O_5$ between 1:1 and 2:1.

When a precipitation inhibitor is present in a potentially scale-forming system at a markedly lower concentration than that required for sequestering (stoichiometric) the scale-forming cation, it is said to be present in "threshold" amounts. See for example, Hatch and Rice, "Industrial Engineering Chemistry", Vol. 31, pages 51 to 53 (January 1939); Reitemeier and Buehrer, "Journal of Physical Chemistry", Vol. 44, No. 5, pages 535 to 536 (May 1940); Fink and Richardson, U.S. Pat. No. 2,358,222; and Hatch, U.S. Pat. No. 2,539,305.

Generally, sequestering takes place at a weight ratio of threshold active compound greater than scale-forming cation components. Threshold inhibition generally takes place at a weight ratio of threshold active compound to scale-forming cation components of less than about 0.5:1.0.

One group of compounds that have shown promise in preventing calcium carbonate and other forms of scale are the N-bis(phosphonomethyl) amino acids which contain either carboxylate or sulfonate groups. These compounds and their use in scale inhibition is described in U.S. Pat. No. 5,087,376. These compounds are prepared using amino acids which are reacted with phosphoric acid and formaldehyde to introduce on to the primary amino group a (bis)phosphonomethyl moiety. This reaction to place phosphonomethyl groups on to amino groups is well documented in U.S. Pat. No. 3,228,846 as well as in U.S. Pat. No. 5,087,376. The disclosures of these patents are incorporated herein by reference.

SUMMARY OF THE INVENTION

Figure 1:
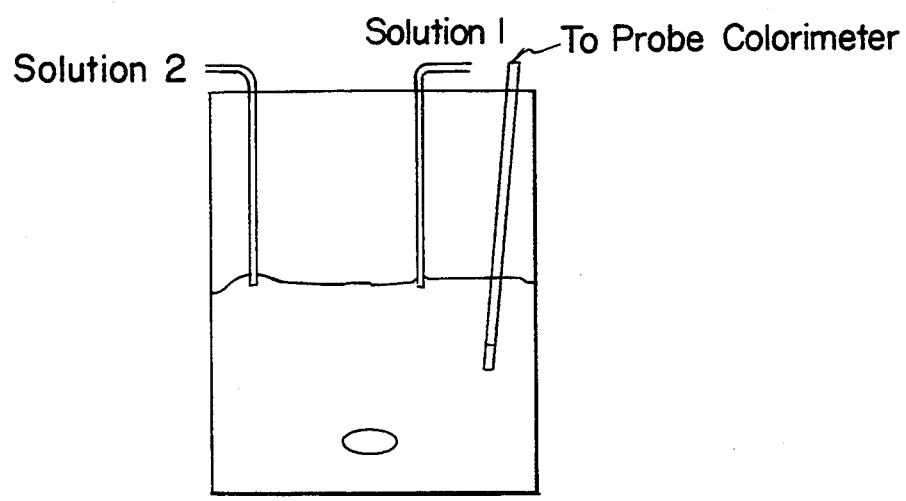
FIG. 1 shows the test set-up of a titration vessel used to evaluate the invention.

The invention relates to certain new N-bis(phosphonomethyl) amino acids which contain either carboxylic acid or sulfonic acid groups. It also relates to the control of calcium carbonate scale on metal surfaces in contact with scale forming industrial process waters.

THE INVENTION

The invention comprises novel N-bis(phosphonomethyl) amino acid from the group consisting of:

A. N,N-bis(phosphonomethyl) L-glutamic acid;
B. N,N-bis(phosphonomethyl) sulfanilic acid;
C. N,N-bis(phosphonomethyl) aniline-2-sulfonic acid;
D. N,N-bis(phosphonomethyl) L-serine; and,
E. N,N,N'-bis(phosphonomethyl) L-lysine The invention also comprises the use of these novel compounds to control calcium carbonate scale on metal surfaces in contact with scale forming industrial process waters. This is accomplished by using the compounds at dosages ranging from as little as 1 up to about 50 ppm by weight of the scale forming water. Good scale inhibition is often achieved using dosages ranging between 1–25 ppm.

All the compounds described above were prepared using the methods shown in detail in U.S. Pat. No. 3,288,846 and 5,087,376.

EVALUATION OF THE INVENTION

To illustrate the ability of the compounds of the invention to prevent calcium carbonate scale, the below described test method was employed.

Using this test method N-bis(phosphonomethyl) amino acids A–E were evaluated. These results are set forth in Table 1.

Dual Mixed Titrant Test

A. SCOPE

This method is used to determine simultaneously the level of hardness and alkalinity that an inhibitor is able to stabilize. This test method can be used to determine if a compound has activity as a $CaCO_3$ scale inhibitor. The ratio of calcium:alkalinity is 1.0 in this test, but could be varied as needed.

B. THEORY

This method involved the simultaneous titration of two solutions. The first solution contains the hardness, while the second solution contains alkalinity. The test is used to determine the ability of an inhibitor to stabilize calcium carbonate. As the concentration of calcium and alkalinity increases beyond the ability of the inhibitor, calcium carbonate precipitates, and is detected by turbidity. Since magnesium is known to affect the precipitation of calcium carbonate, the hardness titrant solution contains both calcium and magnesium at a 2:1 Ca:Mg ratio. The second solution contains the alkalinity. The total alkalinity concentration is equal to the calcium concentration. However, the alkalinity solution is composed of both sodium carbonate and sodium bicarbonate in order to control the pH. The use of the conjugate acid/base pair allows the pH to be controlled strictly using the ratio of bicarbonate to carbonate. The amounts given in this procedure yield a pH of 9.6 at room temperature; the theoretical pH of 10.0 is not achieved due to the presence of carbon dioxide.

C. EQUIPMENT

1. Masterflex Pump with capability for two pump heads. Alternatively, any equipment can be used that is capable of providing the addition of two solutions to the titration vessel at the same flow rate.
2. Magnetic stirrer and stir bars.
3. Constant Temperature Bath capable of holding the titrant solutions and the titrant vessels.
4. Photometer or probe colorimeter such as the Brinkman PC-800 Colorimeter.
5. Strip Chart Recorder.
6. Volumetric flasks of various sizes.
7. 400 mL Beakers.

D. SOLUTIONS

1. Alkalinity Solution—Dissolve 2.01 g sodium bicarbonate and 1.27 g sodium carbonate in deionized water in a 100 mL volumetric flask. Dilute to volume with deionized water and mix well. This solution should be prepared daily.
2. Hardness Solution—Dissolve 3.80 g calcium acetate and 2.57 g magnesium acetate 4-hydrate in deionized water in a 100 mL volumetric flask. Dilute to volume with deionized water and mix well.
3. Inhibitor Solutions—Prepare stock solutions of the inhibitor. Typically, 1000 ppm or 2000 ppm solutions based on product actives will yield easily diluted sample test solutions. (1 mL of a 2000 ppm stock inhibitor solution, diluted to 200 mL total volume yields a 10 ppm inhibitor test solution).

E. PROCEDURE

1. Rinse all beakers used for this titration with dilute HCl solution to minimize contamination problems. Rinse well with deionized water before use.
2. Turn on temperature bath. Set temperature to 45° C.
3. Using the appropriate solution of inhibitor, pipette the amount of stock inhibitor solution into a 400 mL beaker. Dilute with deionized water so that the final volume is 200 mL. The concentration of the inhibitor in the test solution is typically 10 ppm, but can range from 5 ppm to 100 ppm. Add the stir bar. Cover the solution with plastic wrap to prevent evaporation. Place in constant temperature bath.
4. Set up the apparatus so that both solutions of titrant as well as the inhibitor test solutions are in the temperature bath. Ensure that the containers with the titrant solutions are covered to prevent evaporation of the solutions, with the resulting increase in concentration. Allow at least 30 minutes for the temperature of the bath and solutions to equilibrate at 45° C.
5. Set up pump to deliver titrant solutions at a flow rate of 0.2 ml/min. Ensure that the tubes are completely filled with 45° C. titrant before beginning the titration. Set up the colorimeter so that the probe deposition of particulates on the probe is minimized. (See FIG. 1.) Begin stirring at a rate which does not cause bubbles in the optical path of the probe, but provides adequate stirring.
6. Set the wavelength of the colorimeter to 420 nm.
7. Set up the strip chart recorder to record the output from the colorimeter. Using the Brinkman PC-800 Colorimeter, and the above rate of titrant addition, set the chart recorder speed to 2 mm/min. and the sensitivity to 1 Volt Full Scale.
8. Titrate the test solution using the two titrants, while recording the output on the strip chart recorder.
9. After each titration, dip the probe tip and the ends of the titrant tubes into dilute HCl solution and rinse well with deionized water.

F. CALCULATIONS

Figure 2:
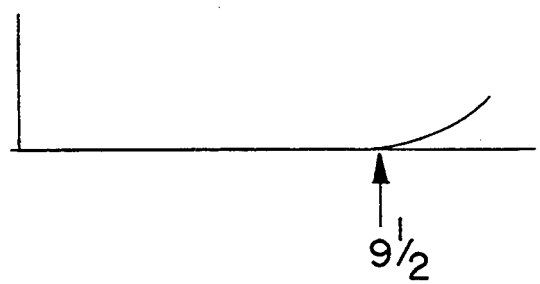
FIG. 2 shows a typical titration curve obtained using the test method used to evaluate the novel compounds of the invention.

A curve similar to that shown in FIG. 2 should be obtained. The endpoint is indicated by the point at which the curve deviates from the vertical line, as shown in FIG. 2. The results are reported as the concentration of Ca at this point, using the following equation.

$$\text{Concn Ca (as CaCO}_3\text{)} = \frac{24 \text{ mg/ml} \times 0.2 \text{ml/min} \times (\text{Distance on Chart/Chart Recorder Speed})}{0.2L + 0.0004L/\text{min} \times (\text{Distance on Chart/Chart Recorder Speed})}$$

G. REPRODUCIBILITY DATA

The reproducibility of the test is shown in the data given for 10 ppm PBTC and a blank.

Blank      166, 154, 154, 166, 177, 177
Mean = 165.7    SD = 10.3 Rel SD = 6.2%

10 ppm PBTC    406, 406, 372, 395, 406
Mean = 396.7    SD = 13.2 Rel SD = 3.3%

The pooled standard deviation from the above data was 11.7. Thus 3 times the standard deviation is 35.

H. LIMITATIONS

The turbidity is assumed to arise from calcium carbonate. The test does not differentiate other species which form precipitates (for example the Ca-inhibitor salt).

TABLE 1

| INHIBITOR | ppm Ca2+ (asCaCO$_3$) at ENDPOINT |
|---|---|
| Blank | 158 |
| 10 ppm C | 395 |
| 10 ppm D | 389 |
| 10 ppm E | 383 |
| 10 ppm B | 378 |
| 10 ppm A | 338 |
| | All values ± 16 ppm |

I claim:
1. N,N-bis(phosphonomethyl) L-serine.
2. N,N,N'N'-bis(phosphonomethyl) L-lysine.

* * * * *